(12) United States Patent
Kim et al.

(10) Patent No.: US 10,787,497 B2
(45) Date of Patent: Sep. 29, 2020

(54) CANCER TREATMENT COMPOSITION FOR INHIBITING TUMOR ANGIOGENESIS, CONTAINING VEGF DEEP BLOCKER

(71) Applicant: IBENTRUS, Inc., Daejeon (KR)

(72) Inventors: Hoeon Kim, Seongnam-si (KR); Hyun-ju Lee, Daejeon (KR)

(73) Assignee: IBENTRUS, INC., Daejeon (KR)

( * ) Notice: Subject to any disclaimer, the term of this patent is extended or adjusted under 35 U.S.C. 154(b) by 0 days.

(21) Appl. No.: 16/311,822

(22) PCT Filed: Jul. 5, 2016

(86) PCT No.: PCT/KR2016/007231
§ 371 (c)(1),
(2) Date: Dec. 20, 2018

(87) PCT Pub. No.: WO2018/008772
PCT Pub. Date: Jan. 11, 2018

(65) Prior Publication Data
US 2019/0375821 A1    Dec. 12, 2019

(51) Int. Cl.
| | | |
|---|---|---|
| A61K 38/16 | (2006.01) | |
| C07K 14/71 | (2006.01) | |
| C07K 16/46 | (2006.01) | |
| A61P 35/00 | (2006.01) | |
| A61K 38/00 | (2006.01) | |

(52) U.S. Cl.
CPC .............. *C07K 14/71* (2013.01); *A61P 35/00* (2018.01); *A61K 38/00* (2013.01); *C07K 2319/00* (2013.01)

(58) Field of Classification Search
None
See application file for complete search history.

(56) References Cited

U.S. PATENT DOCUMENTS

| | | |
|---|---|---|
| 2008/0241142 A1 | 10/2008 | Alitalo et al. |
| 2010/0331250 A1 | 12/2010 | Zhou et al. |
| 2011/0243912 A1 | 10/2011 | Alitalo et al. |
| 2012/0028880 A1 | 2/2012 | Pasqualini et al. |

FOREIGN PATENT DOCUMENTS

| | | |
|---|---|---|
| JP | 2011-512851 | 4/2011 |
| JP | 2014-506572 | 3/2014 |
| KR | 10-0704127 | 4/2007 |
| KR | 10-1397088 | 5/2014 |
| WO | 2005087808 | 9/2005 |
| WO | 2009-112245 | 9/2009 |
| WO | 2011-143408 | 11/2011 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Arber et al. (2016). Blood 127:2391-2405.*
Swerdlow et al. (2016). Blood 127:2375-2390.*
Jocelyn Holash et al., "VEGF-Trap: A VEGF blocker with potent antitumor effects", Proceedings of the National Academy of Sciences (PNAS), US, vol. 99, No. 17, Aug. 20, 2002, pp. 11393-1398.
Jung-Eun Lee et al., "Novel Glycosylated VEGF Decoy Receptor Fusion Protein, VEGF-Grab, Efficiently Suppresses Tumor Angiogenesis and Progression", Molecular Cancer Therapeutics, vol. 14, No. 2, Dec. 22, 2014, pp. 470-479.
Lily Liu, "A novel engineered VEGF blocker with an excellent pharmacokinetic profile and robust anti-tumor activity", BMC Cancer, vol. 15, No. 1, Dec. 25, 2015.
EPO, Supplementary European Search Report of EP 16908214.6 dated Nov. 15, 2019.
S. D. Finley et al., "Compartment model predicts VEGF secretion and investigates the effects of VEGF Trap in tumor-bearing mice", vol. 3, No. 2, article 196, Frontiers in Oncology, Jul. 30, 2013.
M. W. Steward, "Aflibercept (VEGF-TRAP): The Next Anti-VEGF Drug", Inflammation & Allergy—Drug Targets, 2011, vol. 10, pp. 497-508.
T. Arcondeguy et al., "VEGF-A mRNA processing, stability and translation: a paradigm for intricate regulation of gene expression at the post-transcriptional level", Nucleic Acids Research, vol. 41, No. 17, 2013, pp. 7997-8010.
P. Carmeliet, "Angiogenesis in life, disease and medicine", Nature, vol. 438, 2005, pp. 932-936.
N. Ferrara, "The role of VEGF in the regulation of physiological and pathological angiogenesis", Mechanisms of Angiogenesis, 2005, EXS 209-231.
N. Bhagat et al., "Diabetic Macular Edema: Pathogenesis and Treatment", Survey of Ophthalmology, vol. 54, No. 1, 2009, pp. 1-32.
K. A. Houck et al., "The vascular endothelial growth factor family: identification of a fourth molecular species and characterization of alternative splicing of RNA", Mol. Endocrinol. vol. 5, No. 12, 1991, pp. 1806-1814.

(Continued)

*Primary Examiner* — Christine J Saoud
*Assistant Examiner* — Jon M Lockard
(74) *Attorney, Agent, or Firm* — Lex IP Meister, PLLC (57) ABSTRACT

The present invention relates to a cancer treatment composition for inhibiting angiogenesis, and a preparation method therefor. An angiogenesis inhibitor according to the present invention is a cancer treatment composition comprising a fusion protein comprising a vascular endothelial growth factor-binding domain of vascular endothelial growth factor receptor 1 (VEGFR1) and a b1 domain of neuropilin-1 (NRP1). The novel fusion protein is an angiogenesis inhibitor for blocking the binding of VEGF to a receptor in the cell membrane, and has an effect of inhibiting the proliferation of cancer cells and the growth and metastasis of cancer. In addition, the fusion protein can be used as an anti-cancer agent and exhibits an effective anti-cancer effect at a lower dose than that of a conventional angiogenesis inhibitor.

10 Claims, 3 Drawing Sheets

Specification includes a Sequence Listing.

(56) References Cited

OTHER PUBLICATIONS

P. Vempati et al., "Formation of VEGF isoform-specific spatial distributions governing angiogenesis: computational analysis", BMC Systems Biology, vol. 5, No. 59, 2011.
K. A. Houck et al., "Dual regulation of vascular endothelial growth factor bioavailability by genetic and proteolytic mechanisms", The Journal of Biological Cemistry, vol. 267, No. 36, 1992, pp. 26031-26037.
P. Carmeliet, "VEGF as a key mediator of angiogenesis in cancer", Oncology, vol. 69 (Suppl. 3), 2005, pp. 4-10.
N. Ferrara et al., "The biology of VEGF and its receptors", Nature Medicine, vol. 9, No. 6, 2003, pp. 669-676.
N. Ferrara, "Role of vascular endothelial growth factor in the regulation of angiogenesis", Kidney International, vol. 56, 1999, pp. 794-814.
N. Ferrara, "VEGF and the quest for tumour angiogenesis factors", Nature Reviews, Cancer, vol. 2, 2002, pp. 795-803.
J. Folkman, "Angiogenesis in cancer, vascular, rheumatoid and other disease", Nature Medicine, vol. 1, No. 1, 1995, pp. 27-31.
M.W. Stewart, "Aflibercept (VEGF Trap-eye): the newest anti-VEGF drug", Br J Ophthalmol, vol. 96, No. 9, pp. 1157-1158.

\* cited by examiner

Expression of VEEP Fusion Protein

FIG. 3

Anticancer Effect

LLC Mouse Model

FIG. 4

End Point Analysis

CANCER TREATMENT COMPOSITION FOR INHIBITING TUMOR ANGIOGENESIS, CONTAINING VEGF DEEP BLOCKER

TECHNICAL FIELD

The present invention relates to a novel angiogenesis inhibiting fusion protein that inhibits cancer growth and metastasis, and a method for producing the same.

BACKGROUND ART

Angiogenesis is an essential process for the proper growth and repair of organs and a highly elaborately regulated process. The regulatory imbalance of these processes results in inflammatory, cardiovascular, immune or malignant diseases. Vascular endothelial growth factor A (VEGFA) is a major inducer of angiogenesis and is known to be involved in cancer growth and progression. VEGFA genes comprise 8 exons and produce at least six major VEGFA isoforms, VEGFA-121, VEGFA-145, VEGFA-165, VEGFA-183, VEGFA-189, and VEGFA-206. Among them, three major homologous proteins, VEGFA-121, VEGFA-165, and VEGFA-189 are secreted in cells, and their characteristics, bioavailability, and distribution are different from one another. However, it is regarded that their angiogenic functions are generally regulated by $VEGF_{165}$.

VEGFAs bind to two kinds of tyrosine kinase receptors, the VEGF receptor (VEGFR) 1 and VEGFR2, not only to participate in development of neovascularization, but also to prevent apoptosis thereby achieving vascular maintenance. Angiogenesis signaling is mediated by the binding of VEGFA to VEGFR2 (KDR) and a co-receptor, neuropilin-1 (NRP1). Although VEGFR2 is a major receptor involved in angiogenesis and vasculogenesis, VEGFR1 has much higher binding affinity to VEGFA than VEGFR2 does.

The VEGFA expression level is increased by physiologically necessary conditions such as wound healing and hypoxic conditions, and it is also increased in pathological conditions such as proliferative retinopathy, arthritis, psoriasis, and cancer. Furthermore, VEGFA is an important mediator of tumor vasculogenesis, because it induces new blood vessel growth from peripheral blood vessels, allows cancer cells to obtain oxygen and nutrients, and facilitates cancer metastasis.

Many anti-VEGF drugs, such as antibody formulations, aptamers and tyrosine phosphorylation inhibitors, have been developed. Recently, aflibercept (VEGF-trap), which is a fusion protein having high affinity to VEGFA, has been highlighted as next-generation drug. This drug consists of the binding sites to VEGFR1 and VEGFR2.

As related prior arts, Korean Patent Laid-Open No. 1397088 entitled as "A fusion protein for inhibiting both angiogenesis and tumor cell proliferation, and composition comprising the same" discloses a fusion protein comprising an angiogenesis inhibitor and a cancer-specific antibody having treatment effect on gastric cancer or breast cancer.

In a related literature, Regeneron and Bayer HealthCare have reported the results of Phase III clinical trials of VEGF Trap-Eye (aflibercept; brand name, Eylea®) for macular degeneration, which shows that it can achieve treatment effect with lower doses compared with Ranibizumab.

Finely et al. developed a mouse model transplanted with human cancer cells for study of cancer characteristics including cancer growth rate and VEGF secretion, to predict VEGF secretion rate using VEGF-trap, which suggests that it can be used as in vivo cancer model at a preclinical stage.

The present inventors prepared an angiogenesis inhibitor (VEGF Deep Blocker: VEEP) fusion protein, which is a decoy receptor comprising an Ig2 domain of VEGFR1 and a b1 domain of NRP1 so as to bind to VEGFA with higher affinity than VEGF-trap and block VEGFA signal transduction, to complete the present invention.

DETAILED DESCRIPTION OF THE INVENTION

Technical Problem

It is an object of the present invention to provide a novel angiogenesis-inhibiting fusion protein that inhibits cancer growth and metastasis and a method for preparing the same.

It is an object of the present invention to provide a recombinant DNA encoding a novel angiogenesis-inhibiting fusion protein that inhibits cancer growth and metastasis.

Technical Solution

To this end, one aspect of the present invention provides a fusion protein characterized by comprising the Ig2 domain of vascular endothelial growth factor receptor 1 (VEGFR1) and the b1 domain of neuropilin 1 (NRP1). The composition comprising the protein is capable of inhibiting cancer growth and metastasis, and can be used for the treatment of cancer.

Effects of the Invention

The novel fusion protein according to the present invention is an angiogenesis inhibitor that blocks vascular endothelial growth factor from binding to its receptor on the cell membrane, and has an effect of inhibiting cancer cell proliferation, growth, and metastasis. The composition containing the fusion protein can be usefully employed as an anticancer agent. In addition, the composition exhibits a high anticancer effect with a lower dose compared with conventional angiogenesis inhibitors.

MODE FOR THE INVENTION

Hereinafter, the present invention will be described in more detail with reference to Examples. However, these Examples are for illustrative purposes only, and the invention is not intended to be limited by these Examples.

A first embodiment of the present invention provides a fusion protein characterized by comprising an Ig2 domain of vascular endothelial growth factor receptor 1 (VEGFR1) and a b1 domain of neuropilin 1 (NRP1). More specifically, the vascular endothelial growth factor receptor 1 may be represented by, but is not limited to, SEQ ID NO: 1. The Ig2 domain and the b1 domain of neuropilin 1 (NRP1) may be in various forms, and preferably, the Ig2 domain and the b1 domain of neuropilin 1 (NRP1) may be represented by SEQ ID NO: 2. The fusion protein may further comprise a Fc domain of an immunoglobulin, and various Fc domains can be used. Preferably, the Fc domain may be represented by SEQ ID NO: 3. The fusion protein may further comprise a leader sequence for expression, and various leader sequences can be used. Preferably, the leader sequence may be represented by SEQ ID NO: 4. More preferably, the fusion protein may have the amino acid sequence of SEQ ID NO: 5.

A second embodiment of the present invention provides a composition for cancer treatment, the composition comprising the above-described fusion protein. Those skilled in the art may add various forms of drug delivery materials, excipients, stabilizers, and the like, to the composition, and these various formulations also fall within the scope of the present invention.

A third embodiment of the present invention provides a DNA fragment encoding the protein. A person skilled in the art to which the present invention belongs can produce various DNA sequences encoding the fusion protein of the present invention according to the degeneration of the genetic code. Finally, any type of DNA sequence encoding the protein of the present invention may be within the scope of the invention.

A fourth embodiment of the present invention provides a transformant obtained by transformation/transfection using the above recombinant vector. For the transformant, various cells can be used; preferably human-derived cells and most preferably HEK293E cells can be used.

A fifth embodiment of the present invention provides a method of preparing a protein, comprising culturing the transformed cell according to the present invention; and separating the fusion protein from the cell culture media.

DETAILED DESCRIPTION OF THE INVENTION

Method
1. Preparation of VEGFR1-NRP1-Fc Fusion Protein

The DNA fragment encoding Ig2 domain of VEGFR1 was obtained by PCR of the synthesized DNA (Ezbio; EZbio), and the DNA fragment encoding b1 domain of NRP1 was obtained from the human gene bank of the Korea Research Institute of Bioscience and Biotechnology. The DNA fragment comprising the two fragments was linked to human Fc DNA to generate a fusion protein. The cloned DNA was transfected into HEK293E cells and the culture media was purified using Protein A resin. The concentration of the purified protein was calculated by measuring A280 absorbance.

2. In Vitro Affinity Test (ELISA)

VEEP and VEGF-trap were added to a 96-well plate coated with VEGF. After washing several times, HRP-conjugated anti-human Fc was added and stabilized TMB is added thereto, and then, absorbance was measured at 450 nm.

3. VEEP Animal Test

Target disease and solid tumor animal model As an animal model to verify anticancer effect of drugs, six-week-old male C57BL/6 mice were purchased from Koatech (Pyeongtaek City, Korea). The animals were subjected to a week of adaptation period according to the animal experiment ethics regulations. LLC (Lewis lung carcinoma) cell line was purchased from ATCC for the induction of solid tumor in mice.

In Vivo Assay of Anticancer Effect of VEEP and End Point $1 \times 10^6$ LLC cells were subcutaneously injected into right flank region of 6-week-old C57BL/6 mice. 25 mg/kg of VEEP and 25 mg/kg of VEGF-trap was respectively administered subcutaneously every 3 days from $9^{th}$ day after the LLC injection, and the administration was performed 8 times in total. The proliferation of solid tumors was measured every 3-4 days for 30 days and survival of the solid tumor was observed. The size of the solid tumor was measured using an electronic digital caliper to measure length (major axis) and width (minor axis), orthogonally. The volume of solid tumor was calculated by $\Pi 6 \times (\text{length})^2 \times \text{width}$. On day 30, mice were sacrificed and solid tumors were extracted and weighed using a microbalance.

EXAMPLE 1

Fusion Protein

Figure 1:
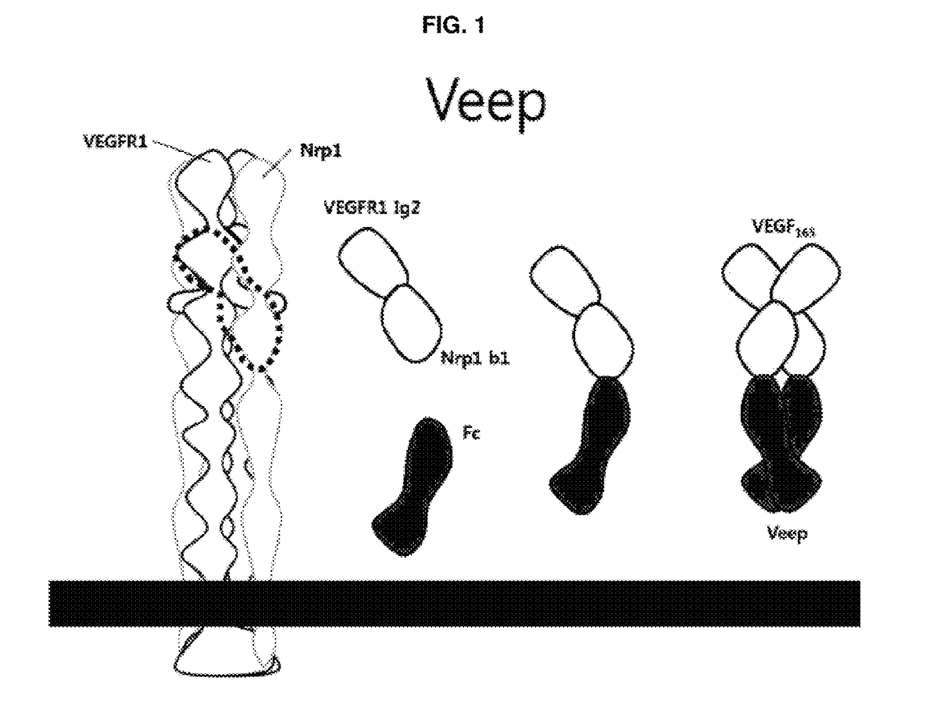
FIG. 1 is a schematic diagram showing a VEGFR1-NRP1-Fc fusion protein.
Figure 2:
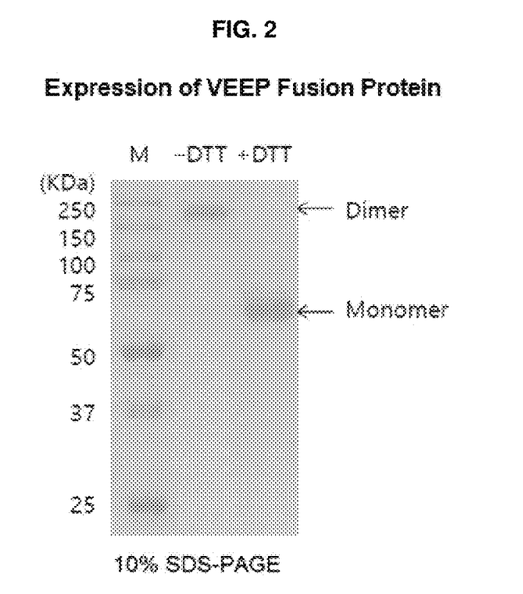
FIG. 2 shows expression of a VEEP fusion protein.

The purified VEGFR1-NRP1-Fc fusion protein was subjected to SDS-PAGE analysis under reducing condition and non-reducing condition, and it was observed that bands for monomer and dimer were shown at the positions corresponding to predicted size (FIG. 2).

EXAMPLE 2

Affinity Analysis

To determine the affinity of VEEP, a fusion protein, to VEGFA, the binding affinity of VEGF to receptor or blocker was analyzed by ELISA analysis. For affinity test, VEG $F_{165}$ was selected among the VEGFA homologous proteins. For controls, comparisons and analyses were conducted using VEGFA receptors naturally expressed in a cell, such as VEGFR1, VEGFR2, NRP1, and NRP2, and commercially available blockers such as VEGF-trap, bevacizumab, and Ranibizumab. The analysis results showed that the binding affinity of VEGF-trap to $VEGF_{165}$ was the highest among the control group. In contrast, VEEP, the fusion protein of the present invention, showed the highest binding affinity to $VEGF_{165}$, compared to all controls, and showed 10-times higher binding affinity than that of VEGF-trap (Table 1).

TABLE 1

| | Binding Affinity | |
|---|---|---|
| | VEGF Binder | Kd for $VEGF_{165}$ (pM) |
| Natural Receptor | VEGFR1 | 33 |
| | VEGFR2 | 100 |
| | NRP1 | 312 |
| | NRP2 | 8000 |
| Blocker | Bevacizumab | 1000 |
| | Ranibizumab | 150 |
| | VEGF-trap | 0.5 |
| | Veep | 0.05 |

EXAMPLE 3

Anticancer Effect Test

Figure 3:
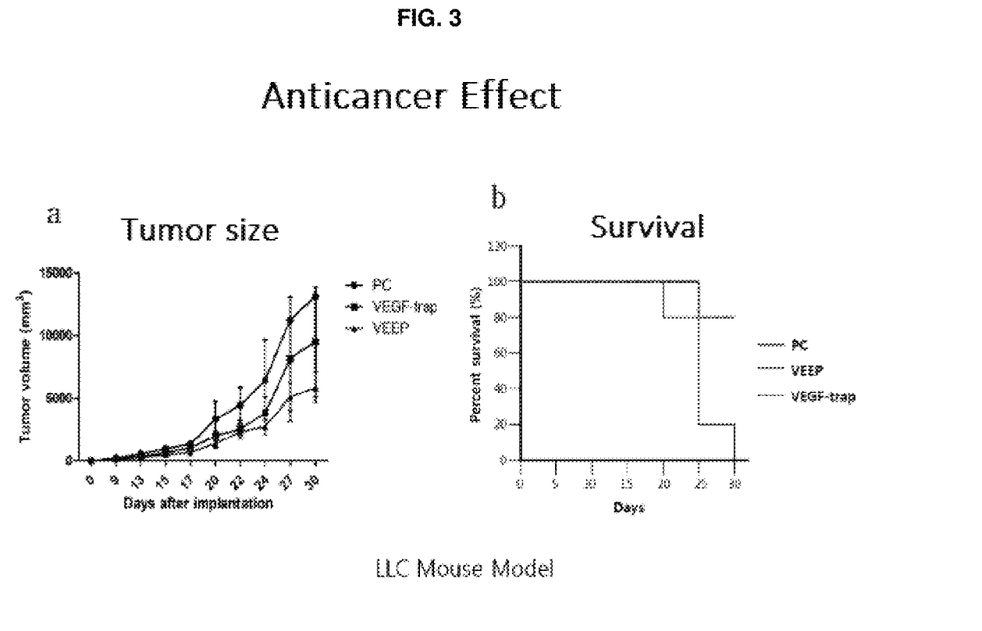
FIG. 3 show results obtained by comparing anticancer effect of VEEP with that of a control VEGF-trap in LLC mouse model.

In order to measure the anti-cancer effect of the VEEP fusion protein prepared and purified according to the present invention, measurement of solid tumor growth and observation of survival were conducted using LLC mouse models. As a result of the measurement of solid tumor growth in LLC mice, the average tumor size in control group without blocker treatment was 13105 mm³. In VEGF-trap-treated group, the average tumor size was decreased to 9479 mm³, but the decrease effect showed large difference between individual mouse models. In contrast, the average size of solid tumors of VEEP-treated mice was measured as 5872 mm³, which shows significant increase in the anti-cancer effect compared to the control without the blocker (FIG. 3). In addition, the anti-cancer effect of VEEP was superior to that of VEGF-trap. The survival rate of VEEP fusion protein-treated mice was 80%, which is superior to that of VEGF-trap-treated control (80%) or blocker non-treated control (0%). Therefore, it is believed that the VEEP fusion protein prepared in the present invention can be usefully applied to patients who cannot be treated with VEGF-trap.

EXAMPLE 4

End Point Analysis

Figure 4:
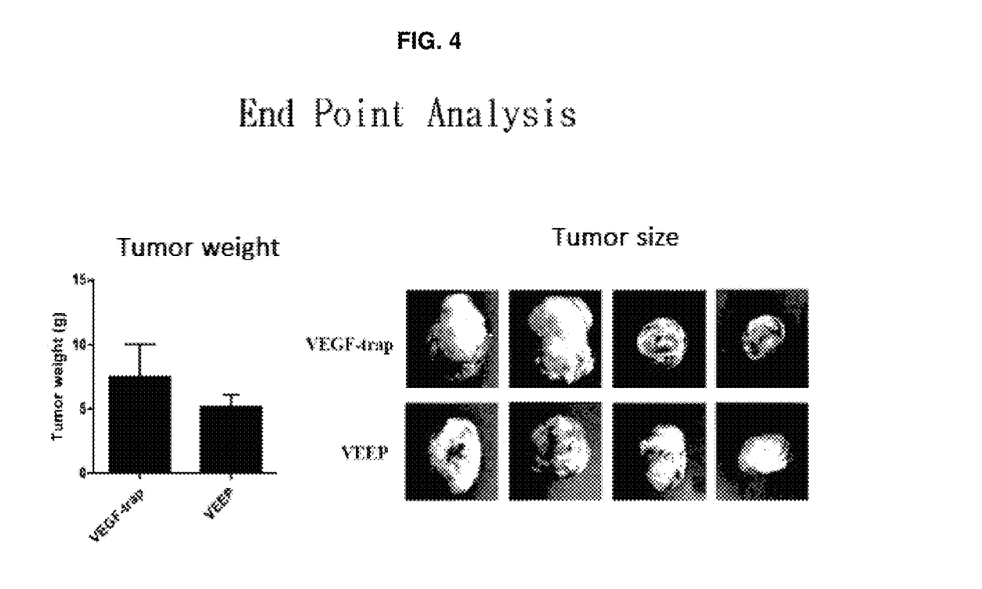
FIG. 4 shows results of endpoint analysis for LLC mouse model at $30^{th}$ day after VEEP treatment.

Tumor size and weight were measured at 30$^{th}$ day after treating LLC mice with VEEP. The solid tumor weight (5.15g) of the VEEP fusion protein-treated LLC mouse was significant decreased in compared with that (7.49 g) of VEGF-trap-treated mouse (FIG. 3). The VEGF-trap-treated mice showed a large variation in tumor size. In the VEEP-treated mice, the average tumor size was smaller than that of VEGF-trap-treated mice, and the tumor size decrease degrees of the VEEP-treated mice were similar to one another (FIG. 4). Thus, as in the results of the above anticancer effect analysis, the VEEP blocker of the present invention is considered to be effectively applied to patients who had no therapeutic effect with VEGF-trap.

REFERENCES

1. Arcondeguy, T., et al. (2013). VEGF-A mRNA processing, stability and translation: a paradigm for intricate regulation of gene expression at the post-transcriptional level. Nucleic Acids Res 41, 7997-8010.
2. Carmeliet, P. (2005) Angiogenesis in life, disease and medicine. Nature 438, 932-936.
3. Ferrara, N. (2005) The role of VEGF in the regulation of physiological and pathological angiogenesis. EXS 209-231.
4. Bhagat, N., et al. (2009)Diabetic macular edema: pathogenesis and treatment. Surv. Ophthalmol. 54(1), 1-32.
5. Houck, K. A., et al. (1991) The vascular endothelial growth factor family: identification of a fourth molecular species and characterization of alternative splicing of RNA. Mol. Endocrinol. 5, 1806.1814.
6. Vempati, P., Popel, A. S. and Mac Gabhann, F. (2011) Formation of VEGF isoform-specific spatial distributions governing angiogenesis: computational analysis. BMC Syst. Biol. 5, 59.
7. Houck, K. A., et al. (1992) Dual regulation of vascular endothelial growth factor bioavailability by genetic and proteolytic mechanisms. J. Biol. Chem. 267, 26031-26037.
8. Carmeliet, P. (2005) VEGF as a key mediator of angiogenesis in cancer. Oncology 69(Suppl. 3), 4-10.
9. Ferrara, N., Gerber, H. P. and LeCouter, J. (2003) The biology of VEGF and its receptors. Nat. Med. 9, 669-676.
10. Ferrara, N. (1999) Role of vascular endothelial growth factor in the regulation of angiogenesis. Kidney Int. 56, 794-814.
11. Ferrara, N. (2002) VEGF and the quest for tumour angiogenesis factors. Nat. Rev. Cancer 2, 795-803.
12. Folkman, J. (1995) Angiogenesis in cancer, vascular, rheumatoid and other disease. Nat. Med. 1, 27-31.
13. Stewart, M. W. (2012). Aflibercept (VEGF Trap-eye): the newest anti-VEGF drug. Br J Ophthalmol 96, 1157-1158.
14. Finley, S. D., Dhar, M., and Popel, A. S. (2013). Compartment model predicts VEGF secretion and investigates the effects of VEGF trap in tumor-bearing mice. Front Oncol 3, 196.

```
SEQ ID NO: 1: Sequence of VEGFR1 part
VSDTGRPFVEMYSEIPEIIHMTEGRELVIPCRVTSPNITVTLKKFPLDT

LIPDGKRIIWDSRKGFIISNATYKEIGLLTCEATVNGHLYKTNYLTHRQ

TNT (VEGFR1)

SEQ ID NO: 2: Sequence of Nrp1 part
SaiakegfSanysvLQSsvsedfkcmealgmesgeihsdqitassqyst nwsaersrlnypengwtpgedsyrewiqvdlgllrfvtavgtqgaiske tkkkyyvktykidvssngedwitikegnkpvlfqgntnptdvvvavfpk plitrfvrikpatwetgismrfevygckit SEQ ID NO: 3: Immunoglobulin Fc domain
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSR

WQQGNVFSCSVMHEALHNHYTQKSLSLSPGK

SEQ ID NO: 4: Leader sequence
MYLGLNYVFIVFLLNGVQS

SEQ ID NO: 5: Full-length sequence
MYLGLNYVFIVFLLNGVQSVSDTGRPFVEMYSEIPEIIHMTEGRELVIP

CRVTSPNITVTLKKFPLDTLIPDGKRIIWDSRKGFIISNATYKEIGLLT

CEATVNGHLYKTNYLTHRQTNTSaiakegfSanysvLQSsvsedfkcme algmesgeihsdqitassqystnwsaersrlnypengwtpgedsyrewi qvdlgllrfvtavgtqgaisketkkkyyvktykidvssngedwitikeg nkpvlfqgntnptdvvvavfpkplitrfvrikpatwetgismrfevygc kitDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVS

LTCLVKGFYPSDIAVEWESNGQPENNYKTTPPVLDSDGSFFLYSKLTVD

KSRWQQGNVFSCSVMHEALHNHYTQKSLSLSPGK
```

The invention claimed is:

1. A fusion protein comprising an Ig2 domain of vascular endothelial growth factor receptor 1 (VEGFR1) consisting of the amino acid sequence of SEQ ID NO: 1, a b1 domain of neuropilin 1 (NRP1) consisting of the amino acid sequence of SEQ ID NO: 2, and an Fc domain of an immunoglobulin, wherein the Ig2 domain of VEGFR1, the b1 domain of NRP1, and the Fc domain are fused in order.

2. The fusion protein of claim 1, wherein the Fc domain consists of the amino acid sequence of SEQ ID NO: 3.

3. The fusion protein of claim 2, which further comprises the amino acid sequence of SEQ ID NO: 4.

4. The fusion protein of claim 3, which comprises the amino acid sequence of SEQ ID NO:5.

5. The fusion protein of claim 1, which further comprises the amino acid sequence of SEQ ID NO: 4.

6. A composition comprising the fusion protein of claim 1 and a pharmaceutically acceptable carrier.

7. A method of treating solid tumors, comprising administering the fusion protein of claim 1 to a patient in need thereof.

8. The method of claim 7, wherein the Fc domain consists of the amino acid sequence of SEQ ID NO: 3.

9. The method of claim 7, wherein the fusion protein further comprises the amino acid sequence of SEQ ID NO: 4.

10. The method of claim 7, wherein the fusion protein comprises the amino acid sequence of SEQ ID NO: 5.

* * * * *

SEQUENCE LISTING

<160> NUMBER OF SEQ ID NOS: 5

<210> SEQ ID NO 1
<211> LENGTH: 101
<212> TYPE: PRT
<213> ORGANISM: Artificial Sequence
<220> FEATURE:
<223> OTHER INFORMATION: Synthetic: Homo sapiens partial VEGFR1

<400> SEQUENCE: 1

```
Val Ser Asp Thr Gly Arg Pro Phe Val Glu Met Tyr Ser Glu Ile Pro
1               5                   10                  15

Glu Ile Ile His Met Thr Glu Gly Arg Glu Leu Val Ile Pro Cys Arg
            20                  25                  30

Val Thr Ser Pro Asn Ile Thr Val Thr Leu Lys Lys Phe Pro Leu Asp
        35                  40                  45

Thr Leu Ile Pro Asp Gly Lys Arg Ile Ile Trp Asp Ser Arg Lys Gly
    50                  55                  60

Phe Ile Ile Ser Asn Ala Thr Tyr Lys Glu Ile Gly Leu Leu Thr Cys
65                  70                  75                  80

Glu Ala Thr Val Asn Gly His Leu Tyr Lys Thr Asn Tyr Leu Thr His
                85                  90                  95

Arg Gln Thr Asn Thr
            100
```

<210> SEQ ID NO 2
<211> LENGTH: 177
<212> TYPE: PRT
<213> ORGANISM: Artificial Sequence
<220> FEATURE:
<223> OTHER INFORMATION: Synthetic: Homo sapiens partial Nrp1 sequence

<400> SEQUENCE: 2

```
Ser Ala Ile Ala Lys Glu Gly Phe Ser Ala Asn Tyr Ser Val Leu Gln
1               5                   10                  15

Ser Ser Val Ser Glu Asp Phe Lys Cys Met Glu Ala Leu Gly Met Glu
            20                  25                  30

Ser Gly Glu Ile His Ser Asp Gln Ile Thr Ala Ser Ser Gln Tyr Ser
        35                  40                  45

Thr Asn Trp Ser Ala Glu Arg Ser Arg Leu Asn Tyr Pro Glu Asn Gly
    50                  55                  60

Trp Thr Pro Gly Glu Asp Ser Tyr Arg Glu Trp Ile Gln Val Asp Leu
65                  70                  75                  80

Gly Leu Leu Arg Phe Val Thr Ala Val Gly Thr Gln Gly Ala Ile Ser
                85                  90                  95

Lys Glu Thr Lys Lys Lys Tyr Tyr Val Lys Thr Tyr Lys Ile Asp Val
            100                 105                 110

Ser Ser Asn Gly Glu Asp Trp Ile Thr Ile Lys Glu Gly Asn Lys Pro
        115                 120                 125

Val Leu Phe Gln Gly Asn Thr Asn Pro Thr Asp Val Val Val Ala Val
    130                 135                 140

Phe Pro Lys Pro Leu Ile Thr Arg Phe Val Arg Ile Lys Pro Ala Thr
145                 150                 155                 160

Trp Glu Thr Gly Ile Ser Met Arg Phe Glu Val Tyr Gly Cys Lys Ile
                165                 170                 175

Thr
```

```
<210> SEQ ID NO 3
<211> LENGTH: 227
<212> TYPE: PRT
<213> ORGANISM: Artificial Sequence
<220> FEATURE:
<223> OTHER INFORMATION: Synthetic: Homo spiens immunoglobulin Fc domain

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 4
<211> LENGTH: 19
<212> TYPE: PRT
<213> ORGANISM: Artificial Sequence
<220> FEATURE:
<223> OTHER INFORMATION: Synthetic: Homo sapiens leader sequence

<400> SEQUENCE: 4

Met Tyr Leu Gly Leu Asn Tyr Val Phe Ile Val Phe Leu Leu Asn Gly
1               5                   10                  15

Val Gln Ser

<210> SEQ ID NO 5
<211> LENGTH: 524
<212> TYPE: PRT
<213> ORGANISM: Artificial Sequence
<220> FEATURE:
<223> OTHER INFORMATION: Synthetic: Fusion protein VEEP6

<400> SEQUENCE: 5
```

```
Met Tyr Leu Gly Leu Asn Tyr Val Phe Ile Val Phe Leu Leu Asn Gly
 1               5                  10                  15

Val Gln Ser Val Ser Asp Thr Gly Arg Pro Phe Val Glu Met Tyr Ser
             20                  25                  30

Glu Ile Pro Glu Ile Ile His Met Thr Glu Gly Arg Glu Leu Val Ile
             35                  40                  45

Pro Cys Arg Val Thr Ser Pro Asn Ile Thr Val Thr Leu Lys Lys Phe
 50                  55                  60

Pro Leu Asp Thr Leu Ile Pro Asp Gly Lys Arg Ile Ile Trp Asp Ser
 65                  70                  75                  80

Arg Lys Gly Phe Ile Ile Ser Asn Ala Thr Tyr Lys Glu Ile Gly Leu
                 85                  90                  95

Leu Thr Cys Glu Ala Thr Val Asn Gly His Leu Tyr Lys Thr Asn Tyr
             100                 105                 110

Leu Thr His Arg Gln Thr Asn Thr Ser Ala Ile Ala Lys Glu Gly Phe
             115                 120                 125

Ser Ala Asn Tyr Ser Val Leu Gln Ser Ser Val Ser Glu Asp Phe Lys
             130                 135                 140

Cys Met Glu Ala Leu Gly Met Glu Ser Gly Glu Ile His Ser Asp Gln
145                 150                 155                 160

Ile Thr Ala Ser Ser Gln Tyr Ser Thr Asn Trp Ser Ala Glu Arg Ser
                 165                 170                 175

Arg Leu Asn Tyr Pro Glu Asn Gly Trp Thr Pro Gly Glu Asp Ser Tyr
                 180                 185                 190

Arg Glu Trp Ile Gln Val Asp Leu Gly Leu Leu Arg Phe Val Thr Ala
             195                 200                 205

Val Gly Thr Gln Gly Ala Ile Ser Lys Glu Thr Lys Lys Lys Tyr Tyr
             210                 215                 220

Val Lys Thr Tyr Lys Ile Asp Val Ser Ser Asn Gly Glu Asp Trp Ile
225                 230                 235                 240

Thr Ile Lys Glu Gly Asn Lys Pro Val Leu Phe Gln Gly Asn Thr Asn
                 245                 250                 255

Pro Thr Asp Val Val Val Ala Val Phe Pro Lys Pro Leu Ile Thr Arg
             260                 265                 270

Phe Val Arg Ile Lys Pro Ala Thr Trp Glu Thr Gly Ile Ser Met Arg
             275                 280                 285

Phe Glu Val Tyr Gly Cys Lys Ile Thr Asp Lys Thr His Thr Cys Pro
             290                 295                 300

Pro Cys Pro Ala Pro Glu Leu Leu Gly Gly Pro Ser Val Phe Leu Phe
305                 310                 315                 320

Pro Pro Lys Pro Lys Asp Thr Leu Met Ile Ser Arg Thr Pro Glu Val
                 325                 330                 335

Thr Cys Val Val Val Asp Val Ser His Glu Asp Pro Glu Val Lys Phe
             340                 345                 350

Asn Trp Tyr Val Asp Gly Val Glu Val His Asn Ala Lys Thr Lys Pro
             355                 360                 365

Arg Glu Glu Gln Tyr Asn Ser Thr Tyr Arg Val Val Ser Val Leu Thr
             370                 375                 380

Val Leu His Gln Asp Trp Leu Asn Gly Lys Glu Tyr Lys Cys Lys Val
385                 390                 395                 400

Ser Asn Lys Ala Leu Pro Ala Pro Ile Glu Lys Thr Ile Ser Lys Ala
                 405                 410                 415

Lys Gly Gln Pro Arg Glu Pro Gln Val Tyr Thr Leu Pro Pro Ser Arg
```

-continued

```
                        420                    425                    430
Glu Glu Met Thr Lys Asn Gln Val Ser Leu Thr Cys Leu Val Lys Gly
            435                    440                    445

Phe Tyr Pro Ser Asp Ile Ala Val Glu Trp Glu Ser Asn Gly Gln Pro
        450                    455                    460

Glu Asn Asn Tyr Lys Thr Thr Pro Pro Val Leu Asp Ser Asp Gly Ser
465                     470                    475                    480

Phe Phe Leu Tyr Ser Lys Leu Thr Val Asp Lys Ser Arg Trp Gln Gln
                485                    490                    495

Gly Asn Val Phe Ser Cys Ser Val Met His Glu Ala Leu His Asn His
                500                    505                    510

Tyr Thr Gln Lys Ser Leu Ser Leu Ser Pro Gly Lys
            515                    520
```